(12) United States Patent
Dietz

(10) Patent No.: US 7,632,314 B2
(45) Date of Patent: Dec. 15, 2009

(54) ADJUSTABLE KNEE TIBIAL TRIAL INSERT

(75) Inventor: Terry L. Dietz, Columbia City, IN (US)

(73) Assignee: DePuy Products, Inc., Warsaw, IN (US)

( * ) Notice: Subject to any disclaimer, the term of this patent is extended or adjusted under 35 U.S.C. 154(b) by 34 days.

(21) Appl. No.: 11/935,827

(22) Filed: Nov. 6, 2007

(65) Prior Publication Data
US 2008/0058946 A1 Mar. 6, 2008

Related U.S. Application Data

(62) Division of application No. 10/997,493, filed on Nov. 24, 2004, now Pat. No. 7,309,363.

(51) Int. Cl.
*A61F 2/38* (2006.01)
(52) U.S. Cl. ............................ 623/20.33; 623/23.47
(58) Field of Classification Search ... 623/20.32–20.33, 623/14.12, 23.47
See application file for complete search history.

(56) References Cited

U.S. PATENT DOCUMENTS

| 5,522,899 | A | * | 6/1996 | Michelson | ............ 606/279 |
| 5,569,263 | A | | 10/1996 | Hein | |
| 5,702,464 | A | | 12/1997 | Lackey et al. | |
| 5,733,292 | A | | 3/1998 | Gustilo et al. | |
| 5,782,832 | A | * | 7/1998 | Larsen et al. | ............ 623/17.11 |
| 6,206,928 | B1 | | 3/2001 | Colleran | |
| 6,258,126 | B1 | | 7/2001 | Colleran | |
| 6,641,614 | B1 | | 11/2003 | Wagner et al. | |
| 6,875,235 | B2 | | 4/2005 | Ferree | |
| 7,083,650 | B2 | * | 8/2006 | Moskowitz et al. | ...... 623/17.11 |
| 7,217,291 | B2 | * | 5/2007 | Zucherman et al. | ...... 623/17.15 |
| 2002/0128716 | A1 | | 9/2002 | Cohen et al. | |
| 2006/0069436 | A1 | | 3/2006 | Sutton et al. | |
| 2006/0069447 | A1 | | 3/2006 | DiSilvestro et al. | |

FOREIGN PATENT DOCUMENTS

WO     9709939     3/1997

OTHER PUBLICATIONS

Graichen, F., Bergmann, G., Rohlmann, A., "Inductively Powered Telemetry System for In Vivo Measurement with Orthopaedic Implants," Biotelemetry XIII, Mar. 26-31, 1995, Williamsburg, Virginia, pp. 75-80.

* cited by examiner

*Primary Examiner*—Corrine McDermott
*Assistant Examiner*—Cheryl Miller
(74) *Attorney, Agent, or Firm*—Barnes & Thornburg LLP

(57) ABSTRACT

An adjustable tibial trial insert includes an upper plate having an upper articular surface and a lower plate. A height-adjustment mechanism of the insert is coupled to and positioned generally between the upper plate and the lower plate and is configured to move between a closed position where the upper and lower plates are adjacent each other and an opened position where the upper and lower plates are spaced-apart from each other in order to adjust a height or thickness of the insert.

15 Claims, 8 Drawing Sheets

ADJUSTABLE KNEE TIBIAL TRIAL INSERT

This is a divisional application of copending U.S. patent application Ser. No. 10/997,493, which was filed on Nov. 24, 2004, now U.S. Pat. No. 7,309,363 the entirety of which is hereby incorporated by reference.

FIELD OF THE DISCLOSURE

The present disclosure relates generally to orthopaedic surgical trial implants, and more particularly to an orthopaedic tibial insert or tray trial.

BACKGROUND

During knee replacement surgery tibial trials, such as tibial trial trays and tibial trial inserts, are used to assist a surgeon in preparing the tibial surface for implantation of the tibial portion of the artificial knee. A surgeon often uses a tibial insert to determine the tibial implant size, to make the appropriate cuts and reams in the bone, and to ensure a proper alignment and tibial component thickness prior to implanting the tibial components themselves, for example.

Such a procedure typically entails making an initial cut on the proximal tibial portion of the knee; determining a preferred size trial tray and/or insert; placing the selected trial tray and/or insert over the tibial surface; and performing a trial reduction to ensure proper tibial component thickness and alignment. If, for example, after performing the trial reduction, the surgeon or other technician determines that the trial insert and/or tray is not of the proper thickness, the trial insert and/or is often removed and replaced with a different trial insert and/or tray having a different thickness. In other applications, one or more spacers or other modular components of the tibial trial insert may be inserted into the trial insert to adjust the thickness. These processes may continue until the appropriate thickness of the trial insert and/or tray is determined.

SUMMARY

The present invention comprises one or more of the features recited in the appended claims or the following features or combinations thereof:

An adjustable tibial trial insert includes an upper plate having an upper articular surface and a lower plate. The tibial trial insert may be used with a tibial tray; therefore, the lower plate may include a lower surface configured to engage a top surface of the tibial tray. A height-adjustment mechanism of the insert is coupled to and positioned generally between the upper plate and the lower plate. The height-adjustment mechanism is configured to move between a closed position where the upper and lower plates are adjacent each other and an opened position where the upper and lower plates are spaced-apart from each other.

The height-adjustment mechanism includes drive means coupled to the upper plate and the lower plate and an actuator coupled to the drive means and to one of the upper and lower plates. The actuator may include a lever pivotably coupled to one of the upper plate and the lower plate. The height-adjustment mechanism may also include a height-adjustment lever pivotably coupled to one of the upper plate and the lower plate at a pivot point. A tie-rod may be coupled to the height-adjustment lever at a distance spaced-apart from the pivot point of the height-adjustment lever such that pivoting movement of the height-adjustment lever about the pivot point moves the tie-rod in a generally lateral direction. The actuator may also include a knob and a link pivotably coupled to the drive means and coupled to the knob for rotation with the knob.

In some embodiments, the drive means of the height-adjustment mechanism may include a first linkage pivotably coupled to the upper plate and the lower plate and a second linkage pivotably coupled to the upper plate and the lower plate.

In other embodiments, the drive means may include a wedge having a first angled surface and a second angled surface. The upper plate may include a lower angled surface slidingly engaged with the first angled surface of the wedge and the lower plate may include an upper angled surface slidingly engaged with the second angled surface of the wedge.

In still other embodiments, the drive means may include a first crossbar coupled to the actuator, pivotably coupled to the upper plate, and pivotably coupled to the lower plate. The drive means may further include a second crossbar pivotably coupled to the upper plate and pivotably coupled to the lower plate. The upper plate may include an upper channel and the lower plate may includes a lower channel such that the first crossbar may be received within the upper channel for sliding movement within the upper channel and the second crossbar may be received within the lower channel for sliding movement within the lower channel. The drive means may also include a third crossbar pivotably coupled to the upper plate, pivotably coupled to the lower plate, and spaced-apart from and generally parallel to the first crossbar. The second crossbar may be positioned between the first and third crossbars.

Illustratively, one of the upper and lower plates may include a calibrated scale to visually indicate a height of the adjustable tibial trial. Further, one of the upper plate and the lower plate may include a cavity and at least a portion of the height-adjustment mechanism may be positioned within the cavity. A slot may be formed in a front surface of one of the upper and the lower plate for communication with the respective cavity. The height-adjustment lever may be received through the slot. Further, the slot may include a plurality of detents formed to receive the height-adjustment lever to lock the height-adjustment lever in a particular position.

In other embodiments, an adjustable tibial trial insert includes an upper plate having an upper articular surface, a lower plate, and a height-adjustment mechanism including drive means coupled to the upper plate and the lower plate for moving the upper plate and the lower plate away from each other. The height-adjustment mechanism also includes a tie-rod pivotably coupled to the drive means and an actuator pivotably coupled at a first pivot point to one of the upper plate and the lower plate and pivotably coupled to the tie-rod at a second pivot point spaced-apart from the first pivot point.

In still other embodiment, an adjustable tibial trial insert includes an upper plate having an upper articular surface, a lower plate, and a non-threaded height-adjustment mechanism including drive means coupled to the upper plate and the lower plate. The drive means is movable between a closed position and an opened position to adjust a height of the insert. The height-adjustment mechanism further includes an actuator coupled to the drive means and to one of the upper and lower plates to move the drive means between the closed and opened positions.

The above and other features of the present disclosure will become apparent from the following description and the attached drawings.

BRIEF DESCRIPTION OF THE DRAWINGS

The detailed description particularly refers to the accompanying figures in which.

DETAILED DESCRIPTION OF THE DRAWINGS

Figure 1:
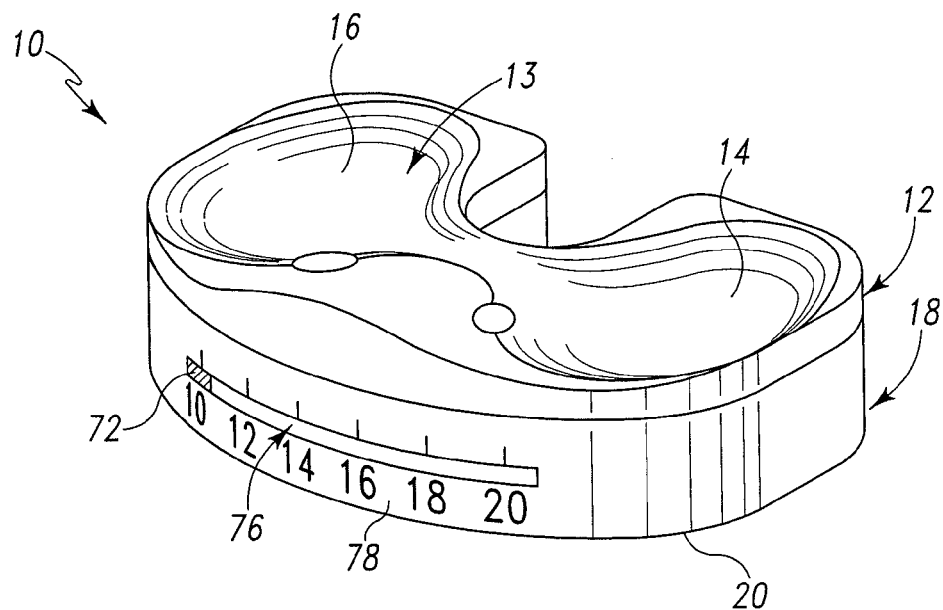
FIG. 1 is a perspective view of the tibial trial insert of the present disclosure shown in a closed position.

An orthopaedic tibial trial insert 10, as shown in FIGS. 1-6, includes an upper plate 12 having an upper articular surface 13 including right and left concave portions 14 and 16 and a lower plate 18 coupled to upper plate 12 and including a lower surface 20 for placement on and engagement with a top surface of an implanted tibial trial tray (not shown), for example. In certain circumstances, the insert 10 may also be placed directly on a surface of the patient's tibia, for example. Insert 10 further includes a height-adjustment mechanism 22 (shown in FIG. 2) coupled to both the upper plate 12 and the lower plate 18 in order to allow a surgeon or other technician to adjust a distance between the upper plate 12 and the lower plate 18 to increase or decrease an overall thickness or height 24 of the insert 10. In the illustrative examples discussed below, the height 24 of the insert is measured from the lower surface 20 of the insert 10 to a low point of the upper articular surface 13.

The height-adjustment mechanism 22 includes drive means or a drive mechanism movable between a closed position and an opened position for adjusting the height of the insert 10 and an actuator coupled to the drive means. As is discussed in greater detail below, the actuator is activated by the surgeon or other technician to move the drive means between the opened and closed positions. Illustratively, in the embodiments disclosed herein, the drive means is coupled to the upper plate 12 and the lower plate 18 and the actuator is coupled to the lower plate 18. However, the actuator may be coupled to the upper plate 12 as well.

As mentioned above, the insert 10 is generally provided for cooperative use with a tibial trial tray (not shown) or a tibial tray implant (not shown). Tibial trays oftentimes include a plate and a stem coupled to the plate and received within a pre-drilled hole in the tibia. The lower surface 20 of the lower plate 18 of the insert 10 is specifically configured to matingly engage and cooperate with an upper surface (not shown) of the tray (not shown). It is the lower surface (not shown) of the plate of the tray, therefore, which is configured to engage and cooperate with a proximal end of the tibia. In some circumstances, however, the lower surface 20 of the lower plate 18 of the insert may be configured to engage and cooperate with the proximal end of the tibia.

Figure 2:
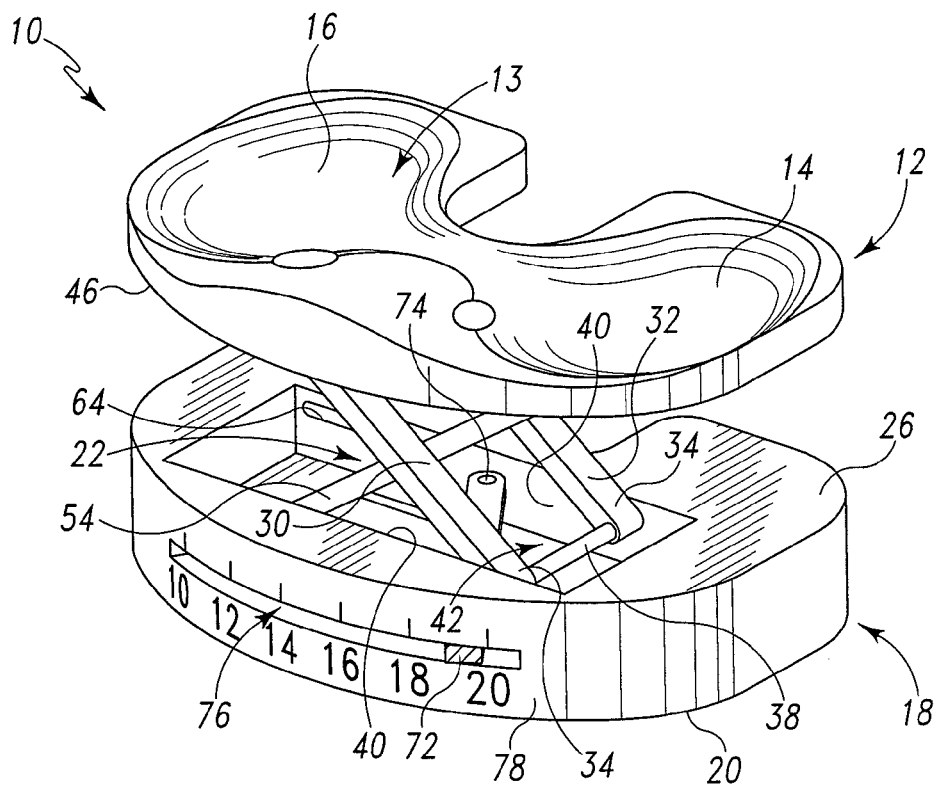
FIG. 2 is a perspective view of the tibial trial insert of FIG. 1 in an opened position and showing a scissors-type height-adjustment mechanism of the insert for adjusting an overall thickness or height of the insert.
Figure 3:
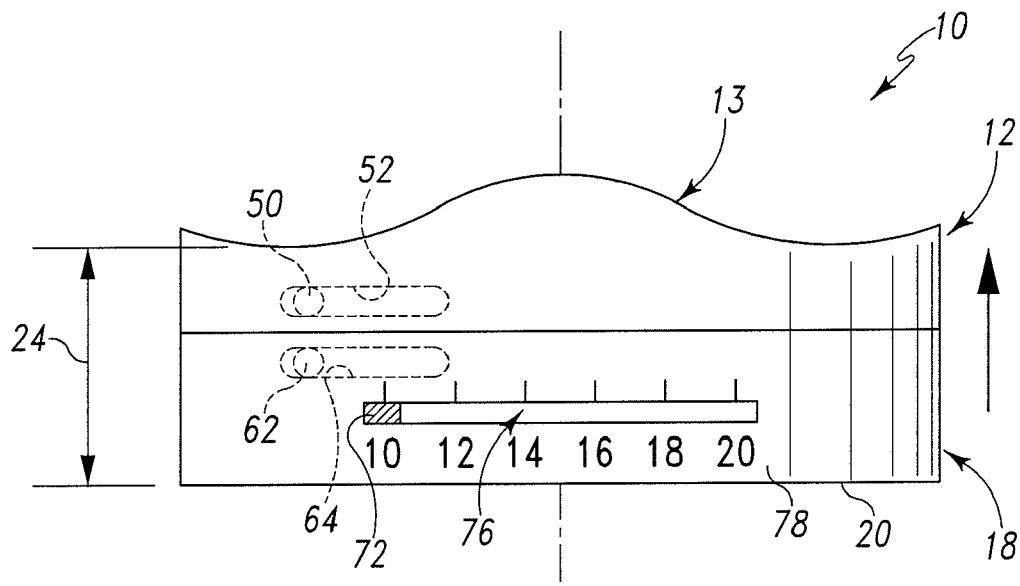
FIG. 3 is a front view of the insert of FIGS. 1 and 2 shown in the closed position.
Figure 4:
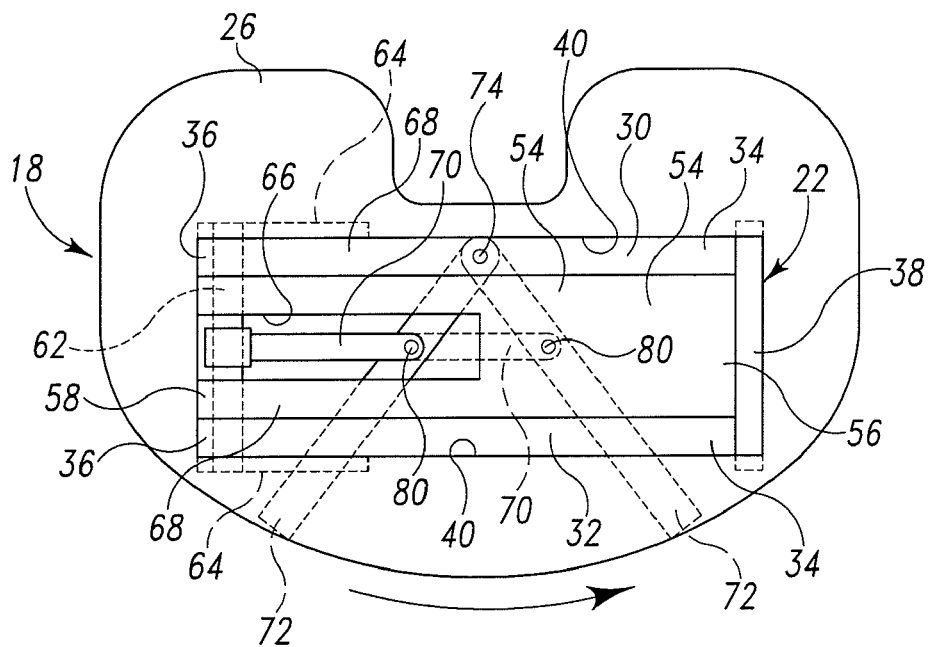
FIG. 4 is a top view of the insert of FIGS. 1-3 with an upper plate of the insert having been removed and showing the adjustment mechanism of the insert in the closed position.
Figure 5:
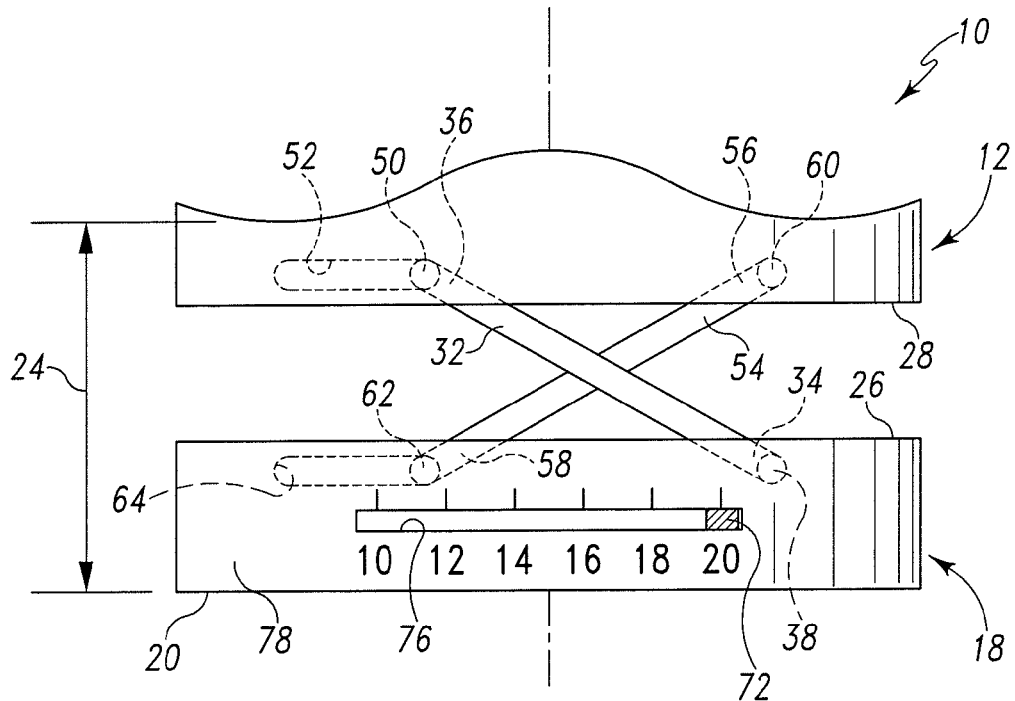
FIG. 5 is a front view, similar to FIG. 3, showing the insert in the opened position.
Figure 6:
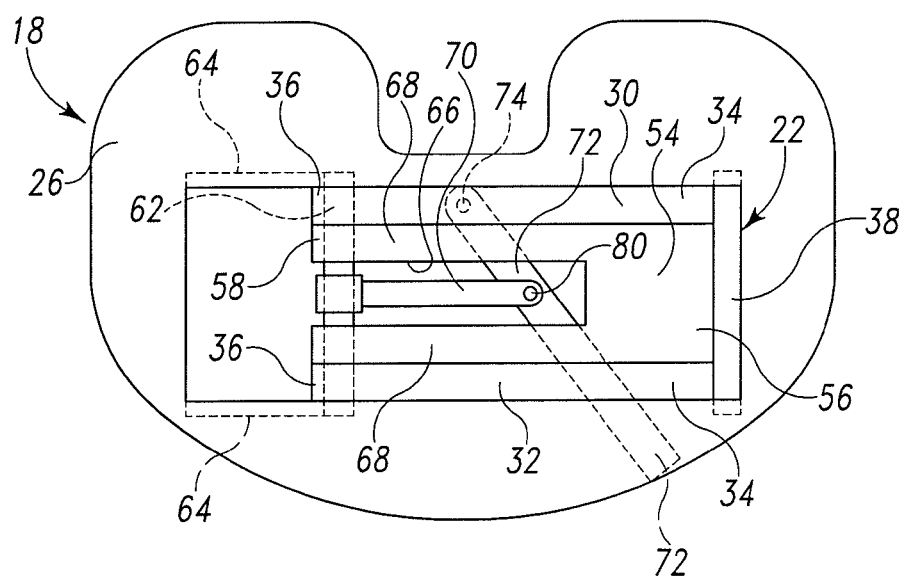
FIG. 6 is a top view similar to FIG. 4 showing the adjustment mechanism of the insert in the opened position.

Looking now to FIGS. 2-6, it may be appreciated that the drive means of the adjustment mechanism 22 is a scissors-type drive means which allows the insert 10 to be moved between a closed position, shown in FIGS. 1, 3, and 4, where the upper and lower plates 12, 18 are generally adjacent to and engaged with each other and an opened position, shown in FIGS. 2, 5, and 6, where the upper and lower plates 12, 18 are spaced-apart from each other. In the closed position, the upper and lower plates 12, 18 may be engaged with each other as is illustratively shown in FIGS. 1, 3, and 4. Alternatively, however, the upper and lower plates 12, 18 may be spaced-apart from each other in the closed position a distance smaller than the spaced-apart distance of the upper and lower plates 12, 18 in the opened position. As mentioned above, the adjustment mechanism 22 allows the surgeon and/or other technicians to adjust an overall height 24 of the insert 10 after the insert 10 has been inserted into the knee of a patient. Illustratively, the insert 10 may remain implanted within the patient while the height 24 of the insert 10 is adjusted.

The adjustment mechanism 22 includes first and second outer crossbars 30, 32 each having a first end 34 coupled to the lower plate 18 and a second end 36 coupled to the upper plate 12. Illustratively, a pivot pin 38 is coupled to the first end 34 each of the first and second outer crossbars 30, 32 and is secured to two opposite, inner walls 40 of the lower plate 18 which define a cavity 42 of lower plate 18, as shown in FIG. 2. The cavity 42 is formed in an upper surface 26 of the lower plate 18 to receive and stow a portion of the adjustment mechanism 22 when the insert 10 is in the closed position to allow the upper surface 26 of the lower plate 18 and a lower surface 28 of the upper plate 12 to engage each other, as shown in FIG. 1. Another cavity (not shown) is formed in lower surface 28 of the upper plate 12 to also receive a portion of the adjustment mechanism 22. Illustratively, at least a portion of the adjustment mechanism 22 is received within the cavity 42 of the lower plate 18 and the cavity (not shown) of the upper plate 12 when the insert 10 is in the opened position as well.

A sliding pin 50 is coupled to the second end 36 of each of the first and second outer crossbars 30, 32, as shown in phantom in FIGS. 3-6. Illustratively, each end of the pin 50 is received within a channel 52 formed within each of two opposite, inner walls (not shown) of the upper plate 12 which define the cavity (not shown) formed in the upper plate 12. As is discussed in greater detail below, the sliding pin 50 slides within the channels 52 as the adjustment mechanism 22 is moved between the closed and opened positions.

The adjustment mechanism 22 also includes a center crossbar 54 positioned between the first and second outer crossbars 30, 32. The center crossbar 54 similarly includes a first end 56 and a second end 58. The first end 56 of the center crossbar 54 is coupled to the upper plate 12 by a pivot pin 60 of the adjustment mechanism 22, as shown in phantom in FIG. 5. The second end 58 of the center crossbar 54 is coupled to the lower plate 18 by sliding pin 62 of the adjustment mechanism 22, as shown in FIGS. 3-6. Similar to the sliding pin 50, each end of the sliding pin 62 is received within a channel 64 formed in each of the opposite inner walls 40 defining the cavity 42 formed in the lower plate 18, as shown in FIG. 2. Further, the sliding pin 62 slides within the channels 64 as the adjustment mechanism 22 is moved between the closed and opened positions.

Looking now to FIGS. 4 and 6, the center crossbar 54 further includes a cut-out portion 66 formed at the second end 36 of the center cross bar 54 to provide two arms 68 of the second end 36 which are each attached to the sliding pin 62. A tie-rod 70 of the adjustment mechanism 22 is positioned between the arms 68 of the center crossbar 54, as shown in FIGS. 4 and 6 and is coupled at one end to the sliding pin 62. The other end of the tie-rod 70 is coupled to a height-adjustment lever 72 which acts as the user-activated actuator to move the adjustment mechanism 22 between the closed and opened positions.

The height-adjustment lever 72 is positioned within the cavity 42 of the lower plate 18 and is pivotably coupled at one end by a pivot pin 74 to the lower plate 18. A free end of the height-adjustment lever 72 is received through a slot 76 formed in a front face 78 of the lower plate 18, as shown in FIGS. 1-3 and 5. Illustratively, the slot 76 is in communication with the cavity 42 of the lower plate 18.

Illustratively, the lever 72 is coupled to the lower plate 18 at a first pivot point and the tie-rod 70 is pivotably coupled to the lever 72 at a second pivot point spaced-apart from the first pivot point. Specifically, as shown in FIGS. 4 and 6, the second pivot point of the second end of the tie-rod 70 and the lever 72 is positioned between the first pivot point of the lever 72 and the free end of the lever 72. Therefore, as the lever 72 is moved counter-clockwise within the slot 76, the tie-rod 70 is pulled to the right and as the lever 72 is moved clockwise within the slot 76, the tie-rod 70 is pushed to the left. Although the lever 72 is coupled to the lower plate 18 and the slot 76 is formed in the lower plate 18, it should be appreciated that the lever 72 may be coupled to the upper plate 12 and the slot 76 may be formed in the upper plate 12 to receive the lever 72 therein.

In use, the height-adjustment lever 72 may be moved within the slot 76 of the lower plate 18 by the surgeon or other technician. Illustratively, as shown in FIGS. 1, 2, 3 and 5, the slot 76 is calibrated at two millimeter intervals between ten and twenty millimeters. Illustratively, the calibrated scale of the slot 76 is calibrated to reflect a combined height of both the height 24 of the insert 10 and a pre-known height or thickness of a tray (not shown) upon which the insert 10 may rest. By knowing the thickness of the tray, therefore, the calibrated scale also visually indicates the height 24 of the insert 10.

When the height-adjustment lever 72 is aligned with the ten millimeter mark, for example, the insert 10 is in the closed position, as shown in FIGS. 3 and 4, and the height 24 of the insert 10 plus a height or thickness of a corresponding tray is approximately ten millimeters. As is discussed above, the illustrative calibrated scale of insert 10 is calibrated to reflect a height or thickness of the insert 10 as well as the pre-known height or thickness of the corresponding tray upon which the insert 10 may rest. Typically, the thickness of a tray may be approximately four millimeters and the scale of the insert 10 is calibrated as such; however, trays having other thickness may be used as well. A recalibrated scale may be used in such circumstances, for example. As such, the calibrated scale is indicative of the height 24 of the insert 10. Further, it is within the scope of the disclosure for the calibrated scale to refer only to the height of the insert 10. When the insert 10 is in the closed position, sliding pins 50 and 62 are positioned at a left-side of each of their respective channels 52, 64 when viewing the insert 10 from the front, as shown in phantom in FIG. 3.

As the surgeon or technician moves the free end of the height-adjustment lever 72 from the left to the right, the tie-rod 70 is pulled (because of its point of attachment to the height-adjustment lever 72 at pivot pin 80) from the left to the right, as shown in FIG. 4. As the tie-bar 70 is moved to the right, the sliding pin 62 within the channel 64 of the lower plate 18 is pulled with the tie-bar 70 to the right as well. As the sliding pin 62 is urged to move to the right, the second end 58 of the center crossbar 54 is urged to move to the right as well. The first end 56 of the center crossbar 54 is therefore urged to pivot about the pivot pin 60 to allow the first end 56 of the center crossbar 54 to move upwardly and raise the upper plate 12 relative to the lower plate 18, as shown in FIGS. 5 and 6, to increase the height 24 of the insert 10.

As the upper plate 12 is moved upwardly to increase the thickness or height 24 of the insert 10, the second end 36 of each of the outer crossbars 30, 32 (which is coupled to the upper plate 12) is urged to move upwardly with the upper plate 12 as well. The sliding pin 50 coupled to the second end 36 of the outer crossbars 30, 32 moves to the right within the channel 52 while the first end 34 of the outer crossbars 30, 32 pivots about pivot pin 38 to remain coupled to the lower plate 18. This movement pulls the second end 58 of the center crossbar 54 to the right, thus driving the scissors-type drive means of the adjustment mechanism 22 open and raising the upper articular surface 13 of the upper plate 12. In general, therefore, adjustment of the insert 10 is provided by sliding the lever 72 to the appropriate thickness setting. As the lever 72 is slid to the right, for example, the sliding pin 62 is pulled to the right within the channel 64 via its connection through the tie-rod 70. This movement pulls the second end 36 of the center crossbar 54 to the right, thus driving the scissors-type drive means of the adjustment mechanism 22 open to raise the upper articular surface 13 of the upper plate 12.

A detent or a plurality of detents (not shown) may be provided within the slot 76 of the lower plate 18 to receive the height-adjustment lever 72 in a locked position. For example, a detent may be formed within the slot 76 at each of the 10, 12, 14, 16, and 20 millimeter thickness settings to receive the lever 72 and secure the insert 10 at the desired height.

Figure 7:
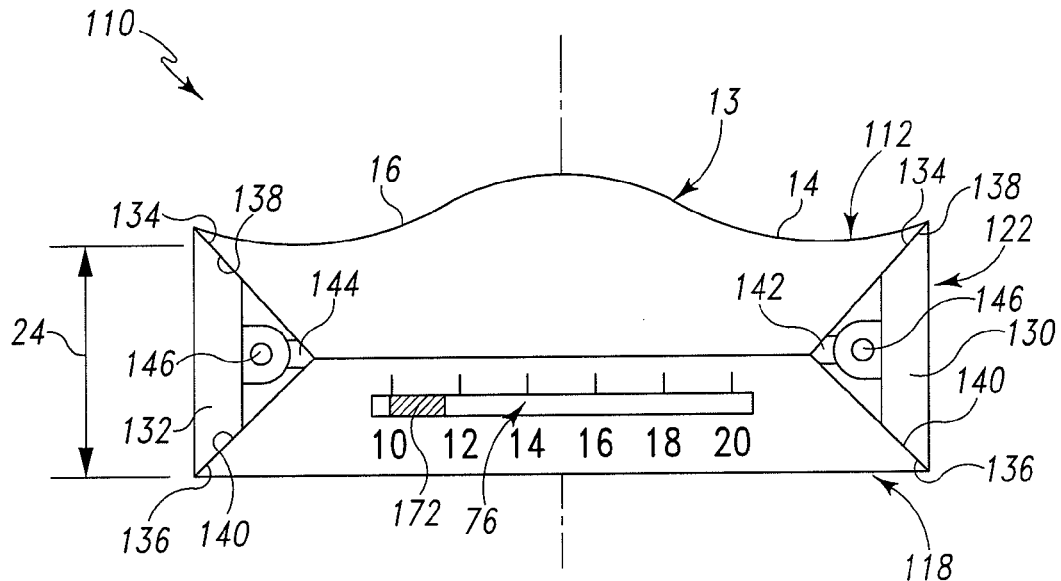
FIG. 7 is a front view of another tibial trial insert of the present disclosure showing a sliding-wedge-type height-adjustment mechanism of the insert for adjusting an overall thickness or height of the insert.
Figure 8:
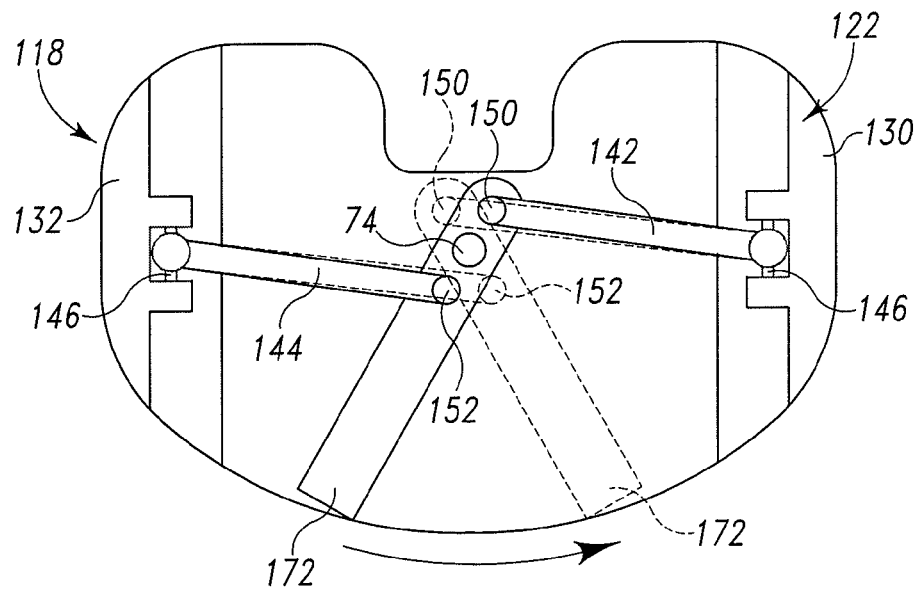
FIG. 8 is a top view of the insert of FIG. 7 with an upper plate of the insert having been removed and showing the adjustment mechanism of the insert in the closed position.
Figure 9:
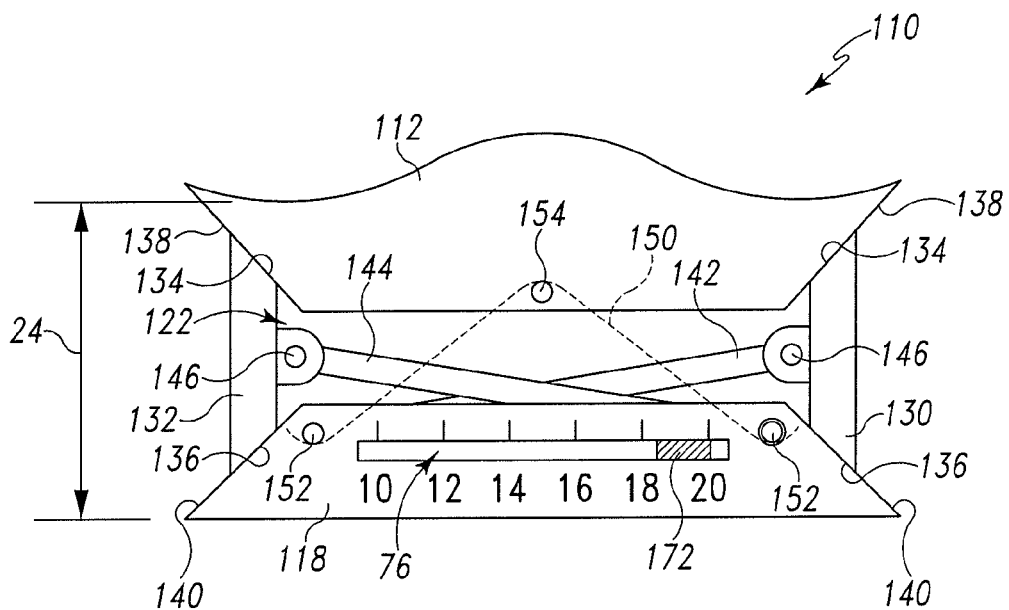
FIG. 9 is a front view of the insert of FIGS. 7 and 8 showing the insert in the opened position.
Figure 10:
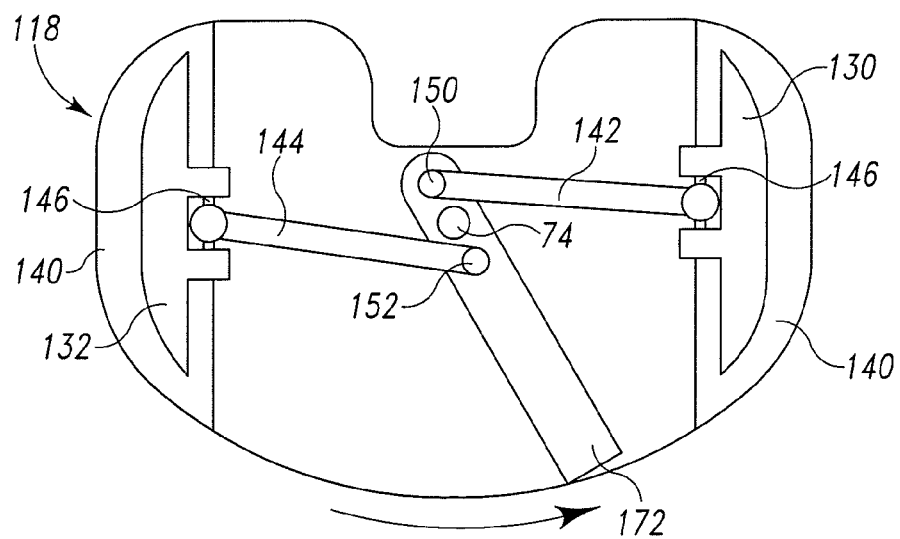
FIG. 10 is a top view of the insert similar to FIG. 8 showing the adjustment mechanism of the insert in the opened position.
Figure 11:
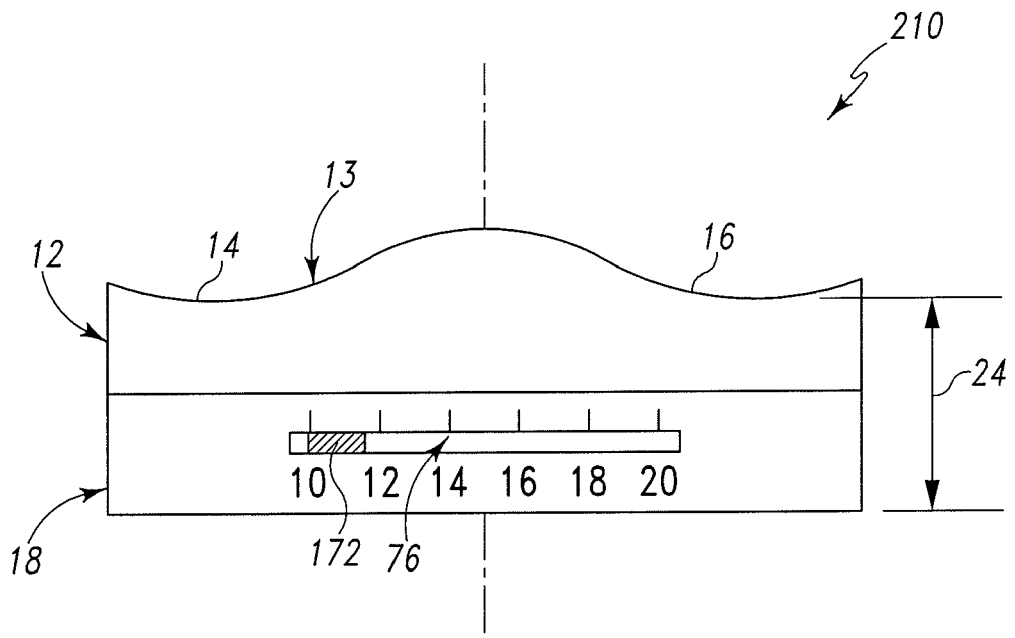
FIG. 11 is a front view of yet another tibial trial insert of the present disclosure showing the insert in the closed position.

Looking now to FIGS. 7-10, another tibial trial insert 110 is provided which is also adjustable between a closed position, shown in FIGS. 7 and 8, and an opened position, shown in FIGS. 9 and 10, in order to adjust the overall height or thickness 24 of the insert 110. Portions of insert 110 are the same as or similar to portions of insert 10; as such, like reference numerals have been used to correspond to like components.

Illustratively, therefore, the insert 110 includes an alternative upper plate 112 having an upper articular surface 13 including concave portions 14, 16 and an alternative lower plate 118. An adjustment mechanism 122 of the insert 110 is positioned between and coupled to both the upper and lower plates 112, 118. Illustratively, the adjustment mechanism 122 shown in FIGS. 7-10 includes a sliding-wedge drive means and an actuator, or lever 172, to move the drive means between the opened and closed positions.

The drive means of the adjustment mechanism 122 includes two sliding wedges 130, 132. Each sliding wedge 130, 132 includes an angled top surface 134 and an angled bottom surface 136. The angled top surface 134 of each of the sliding wedges 130, 132 matingly engages and cooperates with respective outer or lower angled surfaces 138 of the upper plate 112. Similarly, the angled bottom surface 136 of each of the sliding wedges 130, 132 matingly engages and cooperates with respective outer or upper angled surfaces 140 of the lower plate 118, as shown in FIGS. 7 and 9. Additionally, in the illustrative embodiment of FIGS. 7 and 9, the angled top surface 134 of the sliding wedges 130, 132 is oblique to the lower surface of the upper plate 112 and the angled bottom surface 136 of the sliding wedges 130, 132 is oblique to the upper surface of the lower plate. As such, each of the sliding wedges 130, 132 are slidable relative to the upper and lower plates 112, 118 along angled surfaces 138 and 140 of the upper and lower plates 112, 118.

The adjustment mechanism 122 of the insert 110 further includes a first tie-rod 142 coupled to the first sliding wedge 130 and a second tie-rod 144 coupled to the second sliding wedge 132. Illustratively, each tie-rod 142, 144 includes a first end pivotably coupled to the respective wedge 130, 132 by a pin 146 and a second end coupled to a height-adjustment lever 172 of the adjustment mechanism 122. Similar to the height-adjustment lever 72 of the adjustment mechanism 22 described above with reference to FIGS. 1-6, the height-adjustment lever 172 is pivotably coupled to the bottom plate 118 by the pivot pin 74. The lower plate 118 includes a cavity (not shown) formed therein and the adjustment lever is coupled to a bottom wall of the cavity.

Illustratively, as shown in FIGS. 8 and 10, the first tie-rod 142 is pivotably coupled to the lever 172 by a pivot pin 150 at a pivot point spaced-apart from and behind the pivot point of the lever 74. Further, the second tie-rod 144 is pivotably coupled to the lever 172 by a pivot pin 152 at a pivot point spaced-apart from and in front of the pivot point of the lever 74. Therefore, as the lever 172 is pivoted about the pivot point 74 in a counter-clockwise direction, as shown in FIG. 8, the first tie-rod 142 is pulled to the left or toward the center of the insert 110 while the second tie-rod 144 is pulled to the right or toward the center of the insert 110. As each of the respective tie-rods 142, 144 are pulled toward the center of the insert 110, the respective first and second sliding wedges 130, 132 to which each tie-rod 142, 144 is attached are also pulled toward the center of the insert 110.

As shown in FIG. 9, the top angled surface 134 and the bottom angled surface 136 of each sliding wedge 130, 132 acts against the respective angled surfaces 138, 140 of the upper and lower plates 112, 118 to force the upper and lower plates 112, 118 to move away from each other as the sliding wedges 130, 132 are pulled inwardly toward the center of the insert 110. Similarly, as the height-adjustment lever 172 is rotated about its pivot point in a clockwise direction, the tie-rods 142, 144 and the respective sliding wedges 130, 132 are moved away from each other or away from the center of the insert 110 to reduce the distance between the upper and lower plates 112, 118 and thus reduce the overall height 24 of the insert 110.

Similar to the lower plate 12 of insert 10, the lower plate 112 includes a slot 76 for receiving the height-adjustment lever 172. The slot 76 is also calibrated at two millimeter intervals between ten and twenty millimeters. The calibrations provide a visual indication of the overall height 24 of the insert 110. Further, the slot 76 may include detents (not shown) at each calibrated interval (i.e., at 10 millimeters, at 12 millimeters, at 14 millimeters, etc.) to receive the height-adjustment lever 172 and lock the height-adjustment lever 172 at that location and maintain the insert 110 at the desired thickness or height 24.

As shown in FIGS. 7 and 8, the insert 110 is in the closed position such that the upper and lower plates 112, 118 are adjacent each other and the combined thickness 24 of the insert 110 and the tray (not shown) upon which the insert 110 may rest is illustratively 10 millimeters as shown by the height-adjustment lever 172. As shown in FIGS. 9 and 10, on the other hand, the insert 110 is in the opened position such that the upper and lower plates 112, 118 are spaced-apart from each other and the thickness 24 of the insert 110 is set to the largest setting. Illustratively, the height-adjustment lever 172 is positioned at the twenty millimeter mark to represent an overall height including the height 24 of the insert 110 and the height of a tray (not shown) of twenty millimeters.

Although not shown, each of the sliding wedges 130, 132 may be coupled to the upper and lower plates 112, 118 via a tongue-and-groove connection (not shown), for example, between the angled surfaces 134, 136 of the wedges 130, 132 and the angled surfaces 138, 140 of the respective upper and lower plates 112, 118. Alternatively, or in addition to the coupling connection between the wedges 130, 132 and the upper and lower plates 112, 118, the adjustment mechanism 122 may also include a leaf spring 150 to provide a compressive force between the upper plate 112 and the lower plate 118, as shown in phantom in FIG. 9. As discussed above, the wedges 130, 132 are coupled to the lower plate 118 (although the wedges 130, 132 may also be coupled to the upper plate 112). Therefore, the spring 150 provides a compressive force between the upper plate 112 and the lower plate 118 to couple the upper and lower plates 112, 118 together. As such, the spring 150 operates the couple the sliding wedges 130, 132 to both the upper and the lower plates 112, 118.

Illustratively, the lower plate 118 includes two pins or posts 152 spaced-apart from each other and the upper plate 112 includes a single pin or post 154 positioned generally between the posts 152 of the lower plate 118. The leaf spring 150 is threaded under the posts 152 of the lower plate 118 and over the post 154 of the upper plate 112 to urge the upper and lower plates 112, 118 toward each other. The leaf spring 150 or another suitable spring may be provided for the insert 10 shown in FIGS. 1-6 as well to provide a compressive force between the upper and lower plates 12, 18. The adjustment mechanism 122, therefore, acts against the compressive force of the leaf spring 150 when the surgeon or other technician is increasing the thickness 24 of the insert 110, but works with the leaf spring 150 when decreasing the thickness 24 of the insert 110.

Looking now to FIGS. 11-14, another adjustable tibial trial insert 210 is provided. Similar to insert 10, tibial trial insert 210 includes the upper plate 12 and the lower plate 18. Each of the upper and lower plates 12, 18 include cavities (not shown) formed therein to house an adjustment mechanism 222 of the insert 210 for adjusting an overall height of the insert 210. The adjustment mechanism 222 illustratively includes a linkage-style drive means and an actuator to operate the drive means.

Figure 12:
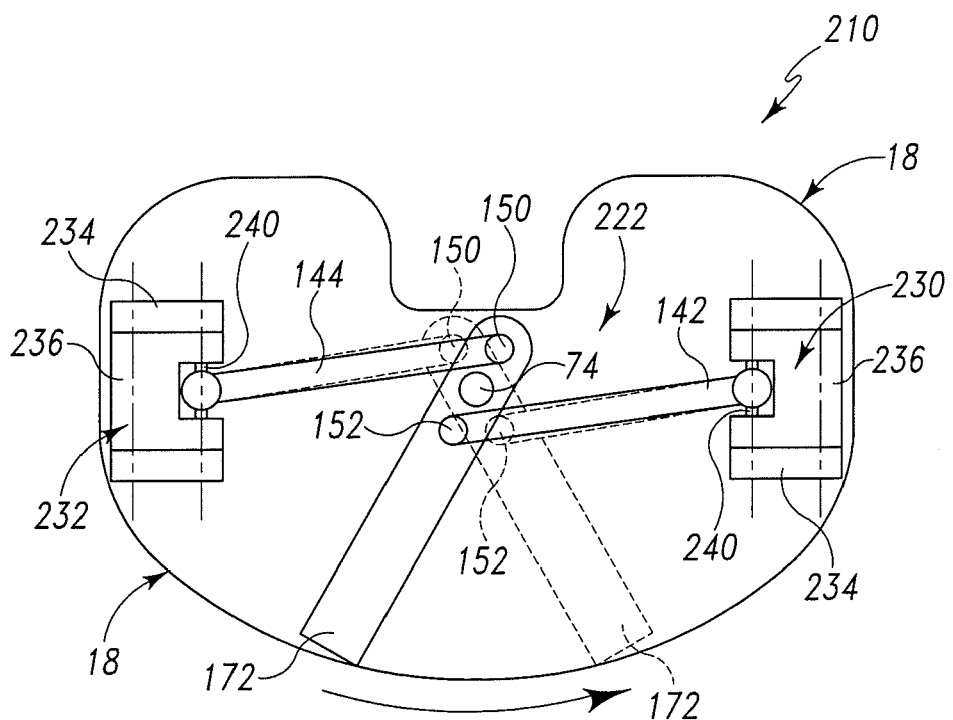
FIG. 12 is a top view of the insert of FIG. 11 with an upper plate of the insert having been removed to reveal a linkage-type height-adjustment mechanism of the insert for adjusting an overall thickness or height of the insert.
Figure 13:
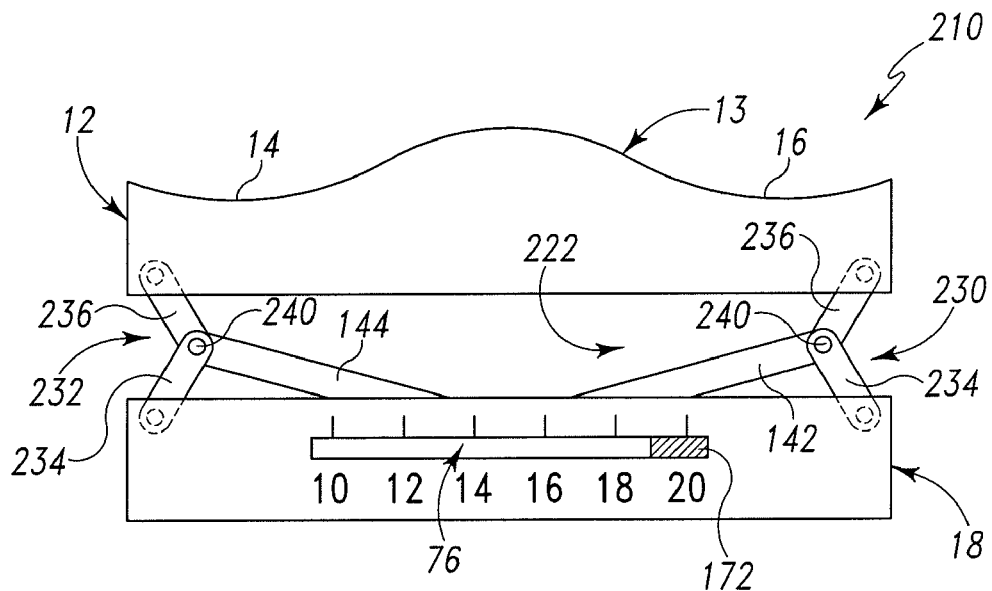
FIG. 13 is a front view of the insert of FIGS. 11 and 12 showing the insert in the opened position.
Figure 14:
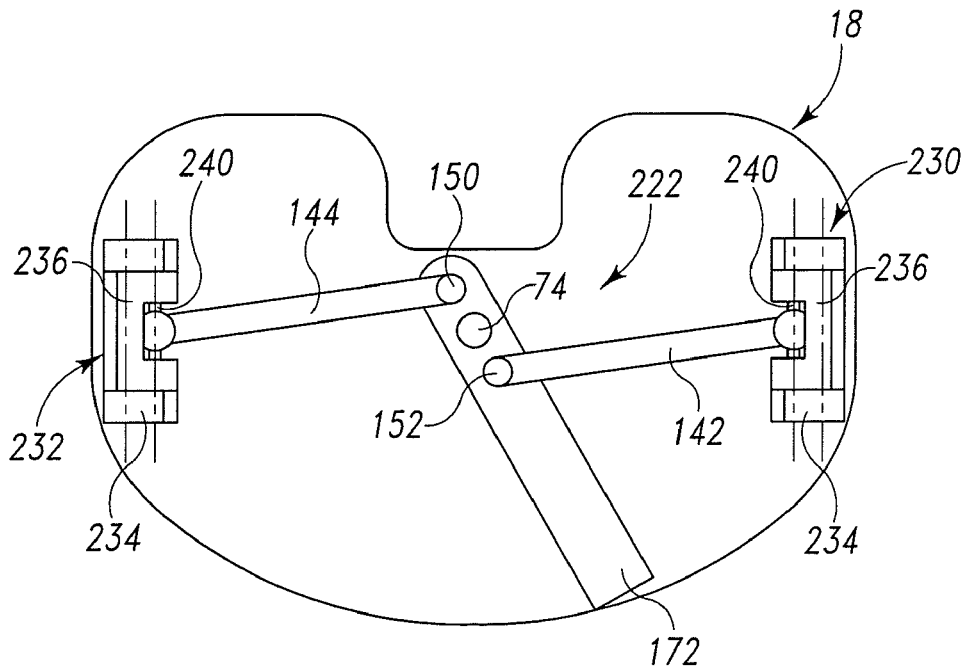
FIG. 14 is a top view of the insert similar to FIG. 12 showing the adjustment mechanism in the fully opened position.

As shown in FIGS. 12-14, the adjustment mechanism 222 includes the height-adjustment lever 172 pivotably coupled to the lower plate 12 by the pivot pin 74, first and second tie-rods 142, 144 coupled to the lever 172, and a first and second linkage 230, 232 coupled to one of the respective tie-rods 142, 144. As shown in FIGS. 12 and 14, the first tie-rod 142 is coupled at its second end by the pivot pin 152 at a pivot point on the lever 172 spaced-apart from and in front of the pivot point 74 of the lever 172 and the second tie-rod 144 is coupled at its second end by the pivot pin 150 at a pivot point on the lever 172 spaced-apart from and behind the pivot point of the lever 172 as viewed from above. As such, the attachment point of the tie-rods 142, 144 to the lever 172 of the adjustment mechanism 222 differs from the attachment point of the tie-rods 142, 144 to the lever 172 of the sliding-wedge adjustment mechanism 122 of the insert 110. Therefore, as opposed to the operation of the sliding-wedge adjustment mechanism 122, counter-clockwise rotation of the lever 172 of the toggle-style drive means of the adjustment mechanism 222 causes the tie-rods 142, 144 to move outwardly away from the center of the insert 210, as shown in FIG. 12.

The second, outermost end of each tie-rod 142, 144 is pivotably coupled to one of the respective linkages 230, 232. Each linkage 230, 232 includes a first link 234 pivotably coupled to the lower plate 18 and a second link 236 pivotably coupled to the upper plate 12. The first and second links 234, 236 of each linkage 230, 232 are also pivotably coupled to each other by a central pin 240. Each tie-rod 142, 144 is also coupled to the central pin 240 of each respective linkage 230, 232. Therefore, as the lever 172 is pivoted in a counter-clockwise direction to increase the height 24 of the insert 210, the tie-rods 142, 144 are pushed outwardly to push the central pin 240 of each linkage 230, 232 outwardly as well as upwardly, as shown in FIG. 13. As the central pin 240 of each linkage 230, 232 is moved outwardly and upwardly, each linkage 230, 232 is moved from a collapsed position toward an expanded position, as shown in FIG. 13, to move the upper plate 12 and the lower plate 18 away from each other, thus increasing the overall thickness 24 of the insert 210.

Similarly, movement of the lever 172 in a clockwise direction pulls the tie-rods 142, 144 toward each other to also pull the center pin 240 of each linkage 230, 232 toward the center of the insert 210 to move each linkage 230, 232 to a more collapsed position. As the linkages 230, 232 move toward a more collapsed position, the upper plate 12 and the lower plate 18 move toward each other to decrease the overall thickness 24 of the insert 310. As with the inserts 10, 110 discussed above, the lower plate 18 of the insert 210 may include detents (not shown) formed in the slot 76 of the lower plate 18 which correspond to a particular height or thickness 24 of the insert 210 to receive the lever 172 therein and secure the insert 210 at that particular desired height.

Figure 15:
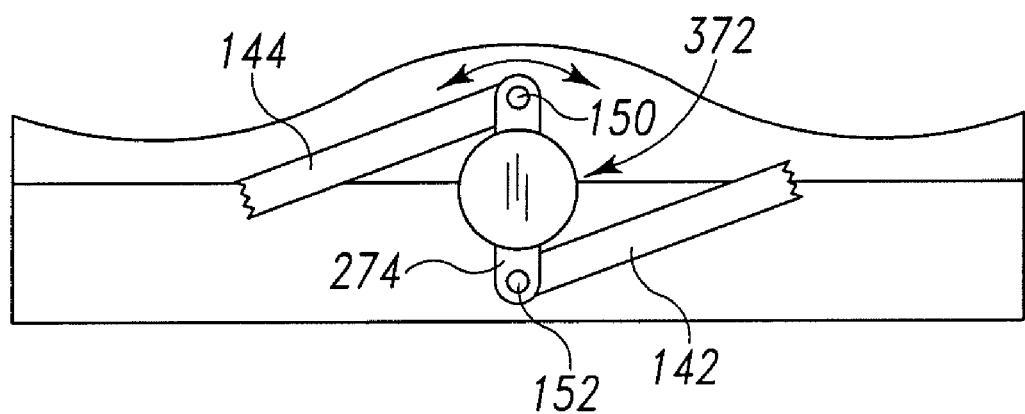
FIG. 15 is a schematic front view of any one of the tibial insert trials disclosed in FIGS. 1-14 showing an alternative rotatable knob actuator of the height-adjustment mechanism.

Although the illustrative actuator of each of adjustment mechanisms 22, 122, 222 described above is the lever 72, 172, other actuators may be used. For example, an alternative actuator such as a knob 372 is shown in FIG. 15. The knob 372 may be used to replace the levers 72, 172 of the adjustment mechanisms 22, 122, 222 described above, for example, to drive the various scissors-type, wedge, and linkage mechanisms of each adjustment mechanism. The knob 272 is mounted to a shaft (not shown) which may extend through the upper or lower plates of the insert. The shaft is then coupled to a vertical bar 274, as shown in FIG. 15, and the second ends of each tie-rod 142, 144 of the adjustment mechanisms 122, 222 or the second end of the tie-rod 70 of the adjustment mechanism 22 are then coupled to one end of the vertical bar 274.

Rotation of the knob 372 causes the tie-rods 70, 142, 144 to pull in or push out depending on the direction of rotation and whether the tie-rods 70, 142, 144 are coupled to the vertical bar 274 above or below its pivot point. For example, if the first tie-rod 142 is coupled to the bottom of the vertical bar 274 below the pivot point of the vertical bar 274 and the second tie-rod 144 is coupled to the top of the vertical bar 274 above the pivot point of the vertical bar 274, clockwise rotation of the knob 272 (and thus the vertical bar 274) pulls the tie-rods 142, 144 toward the center of the insert and counterclockwise rotation of the knob pushes the tie-rods 142, 144 away from the center of the insert. The connection between the tie-rods 142, 144 and the vertical bar 274 may also be switched such that clockwise rotation of the knob 372 pushes the tie-rods 142, 144 away from each other. In either case, the orientation of the tie-rods 142, 144 with respect to the vertical bar 274 may be configured for use with either the sliding wedges 130, 132 and/or the linkages 230, 232. The knob actuator 272 may also be used with the scissors-type drive means of the adjustment mechanism 22 shown in FIGS. 1-6. For example, the tie-rod 70 may be coupled to the vertical bar 274 at a point spaced away from the pivot point of the vertical bar 274 such that rotation of the knob causes the tie-rod 70 to move generally laterally and thus move the center crossbar 54. The knob 372 may also be calibrated to indicate a particular overall height of the trial.

While the concepts of the present disclosure have been illustrated and described in detail in the drawings and foregoing description, such an illustration and description is to be considered as exemplary and not restrictive in character, it being understood that only the illustrative embodiments have been shown and described and that all changes and modifications that come within the spirit of the disclosure are desired to be protected.

There are a plurality of advantages of the concepts of the present disclosure arising from the various features of the systems described herein. It will be noted that alternative embodiments of each of the systems of the present disclosure may not include all of the features described yet still benefit from at least some of the advantages of such features. Those of ordinary skill in the art may readily devise their own implementations of a system that incorporate one or more of the features of the present disclosure and fall within the spirit and scope of the invention as defined by the appended claims.

The invention claimed is:

1. An orthopaedic instrument comprising:
an adjustable tibial trial insert, including:
   (a) an upper plate including (i) an upper articular surface having first and second concave portions configured to receive corresponding femoral condylar surfaces, (ii) a lower surface opposite the upper articular surface; and (iii) a lower angled surface extending from the upper articular surface to the lower surface of the upper plate,
   (b) a lower plate including (i) a lower surface configured to engage a top surface of a tibial tray, (ii) an upper surface opposite the lower surface of the lower plate, and (iii) an upper angled surface extending from the lower surface of the lower plate to the upper surface, and
   (c) a height-adjustment mechanism coupled to and positioned generally between the upper plate and the lower plate and configured to move between a closed position where the upper and lower plates are adjacent each other and an opened position where the upper and lower plates are spaced-apart from each other, wherein the height-adjustment mechanism includes a drive coupled to the upper plate and the lower plate and an actuator coupled to the drive and to one of the upper and lower plates, wherein the drive includes a wedge having a first angled surface slidingly engaged with the upper angled surface and a second angled surface slidingly engaged with the lower angled surface, the wedge being positioned such that the first angled surface is oblique to the lower surface of the upper plate and the second angled surface is oblique to the upper surface of the lower plate.

2. The orthopaedic instrument of claim 1, wherein the height-adjustment mechanism further includes a tie-rod pivotably coupled to the drive at a first end and pivotably couple to the actuator at a second end.

3. The orthopaedic instrument of claim 2, wherein the actuator is pivotably coupled to one of the upper and lower plates at a first pivot point and the tie-rod is pivotably coupled to the actuator at a second pivot point spaced-apart from the first pivot point.

4. The orthopaedic instrument of claim 1, wherein the actuator comprises a lever.

5. The orthopaedic instrument of claim 1, wherein:
the lower plate includes a cavity formed therein, the cavity being defined by a bottom wall of the lower plate, and
the actuator is coupled to the bottom wall of the lower plate.

6. The orthopaedic instrument of claim 5, wherein:
the lower plate includes an anterior side surface extending from the lower surface of the lower plate to the upper surface of the lower plate, the anterior side surface including a slot defined therein, and
the actuator extends through the slot of the lower plate.

7. The orthopaedic instrument of claim 6, wherein the slot of the lower plate is calibrated.

8. The orthopaedic instrument of claim 6, wherein the lower plate includes an inner sidewall defining the slot, the inner sidewall having a plurality of detents to lock the actuator in a first position.

9. The orthopaedic instrument of claim 1, wherein the height-adjustment mechanism further includes a leaf spring positioned to provide an amount of compressive force between the upper plate and the lower plate.

10. The orthopaedic instrument of claim 9, wherein:
the upper plate includes a first post extending therefrom, the lower plate includes a second post and a third post extending therefrom, wherein the leaf spring is coupled to the first, second, and third posts.

11. The orthopaedic instrument of claim 1, wherein:
the lower angled surface of the upper plate is a first lower angled surface and the upper plate further includes a second lower angled surface, each of the first and second lower angled surfaces extending from the upper articular surface to the lower surface of the upper plate,
the upper angled surface of the lower plate is a first upper angled surface and the lower plate includes a second upper angled surface, each of the first and second upper angled surfaces extending from the lower surface of the lower plate to the upper surface of the lower plate,
the wedge of the drive is a first wedge having a first angled surface slidingly engaged with the first upper angled surface of the lower plate and a second angled surface slidingly engaged with the first lower angled surface of the upper plate and the drive further includes a second wedge having a first angled surface slidingly engaged with the second upper angled surface of the lower plate and a second angled surface slidingly engaged with the second lower angled surface of the upper plate,
wherein each of the first and second wedges are positioned such that the first angled surfaces are oblique to the lower surface of the upper plate and the second angled surfaces are oblique to the upper surface of the lower plate.

12. The orthopaedic instrument of claim 11, wherein the actuator is coupled to the first and second wedges.

13. The orthopaedic instrument of claim 11, wherein the height-adjustment mechanism further includes:
a first tie-rod pivotably coupled to the first wedge at a first end and pivotably coupled to the actuator at a second end, and
a second tie-rod pivotably coupled to the second wedge at a first end and pivotably coupled to the actuator at a second end.

14. The orthopaedic instrument of claim 13, wherein:
the first tie-rod is pivotably coupled to the actuator at a first pivot point and the second tie-rod is pivotably coupled to the actuator at a second pivot point spaced apart from the first pivot point.

15. The orthopaedic instrument of claim 14, wherein the actuator is pivotably coupled to one of the upper and lower plates at a third pivot point spaced-apart from the first and second pivot points.

* * * * *